(12) United States Patent
Kirby et al.

(10) Patent No.: US 9,637,766 B2
(45) Date of Patent: May 2, 2017

(54) HOST CELLS AND METHODS FOR PRODUCING 1-DEOXYXYLULOSE 5-PHOSPHATE (DXP) AND/OR A DXP DERIVED COMPOUND

(71) Applicant: The Regents of the University of California, Oakland, CA (US)

(72) Inventors: James Kirby, Berkeley, CA (US); Jeffrey L. Fortman, San Francisco, CA (US); Minobu Nishimoto, El Cerrito, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/186,202

(22) Filed: Jun. 17, 2016

(65) Prior Publication Data

US 2016/0298153 A1    Oct. 13, 2016

Related U.S. Application Data

(62) Division of application No. 13/587,826, filed on Aug. 16, 2012, now Pat. No. 9,382,553.

(60) Provisional application No. 61/524,271, filed on Aug. 16, 2011.

(51) Int. Cl.
| | | |
|---|---|---|
| *C12P 5/00* | (2006.01) | |
| *C12P 19/02* | (2006.01) | |
| *C12N 9/04* | (2006.01) | |

(52) U.S. Cl.
CPC ............ *C12P 19/02* (2013.01); *C12N 9/0006* (2013.01); *C12P 5/007* (2013.01); *Y02P 20/52* (2015.11)

(58) Field of Classification Search
CPC ........ C12N 9/0006; C12P 19/02; C12P 5/007; Y02P 20/52
See application file for complete search history.

(56) References Cited

U.S. PATENT DOCUMENTS

2008/0274523 A1    11/2008 Renninger
2010/0180491 A1    7/2010 Lee

OTHER PUBLICATIONS

Branden et al., Introduction to Protein Structure, Garland Publishing Inc., New York, p. 247, 1991).*
Seffernick et al., J. Bacteriol. 183(8):2405-2410, 2001).*
Witkowski et al., Biochemistry 38:11643-11650, 1999).*
Sadowski et al., Current Opinion in Structural Biology 19:357-362, 2009.*
Eisenreich et al., "Biosynthesis of isoprenoids via the non-mevalonate pathway", CMLS Cell. Mol. Life Sci., 61: 1401-1426, 2004.
Fung et al., "Computational Analysis of the Evolution of 1-Deoxy-d-xylulose-5-phosphate Reductoisomerase, an Important Enzyme in Plant Terpene Biosynthesis", Chem. Biodivesity, 7: 1098-1110, 2010.
Martin et al., "Engineering a mevalonate pathway in *Escherichia coli* for production of terpenoids", Nature Biotechnol., 21(7): 796-802, 2003.
Wungsintaweekul et al., "Phosphorylation of 1-deoxy-D-xylulose by D-xylulokinase of *Escherichia coli* ", Eur. J. Biochem. 268: 310-316, 2001.
Ko et al, "Conversion of Methylglyoxal to Acetol by *Escherichia coli* Aldo-Keto Reductases", J. Bacteriol. 187 (16):5782-5789, 2005.
Perez-Gil et al., "Mutations in *Escherichia coli* aceE and ribB Genes Allow Survival of Strains Defective in the First Step of the Isoprenoid Biosynthesis Pathway", PLOS One 7(8):e43775, Aug. 21, 2012.
Reiling et al., "Mono and Diterpene Production in *Escherichia coli* ", Biotechnol. Bioengin. 87(2):200-212, 2004.
Sauret-Gueto et al., "A mutant pyruvate dehydrogenase E1 subunit allows survivalof *Escherichia coli* strains defective in 1-deoxy-DD-xyluloses-phosphate synthase", FEBS Lett. 580(3):736-740, 2006.
Withers et al., "Identification of Isopentenol Biosynthetic Genes from *Bacillus subtilis* by a Screening Method Based on Isoprenoid Precursor Toxicity", Appl. Environ. Microbiol. 73(19):6277-6283, 2007.

* cited by examiner

*Primary Examiner* — Delia Ramirez
(74) *Attorney, Agent, or Firm* — Robin C. Chiang; Lawrence Berkeley National Laboratory

(57) ABSTRACT

The present invention provides for a genetically modified host cell capable of producing 1-deoxyxylulose 5-phosphate or 1-deoxy-D-xylulose 5-phosphate (DXP) (12), and optionally one or more DXP derived compounds, comprising: (a) a mutant RibB, or functional variant thereof, capable of catalyzing xylulose 5-phoshpate and/or ribulose 5-phospate to DXP, or (b) a YajO, or functional variant thereof, and a XylB, or functional variant thereof.

28 Claims, 8 Drawing Sheets

```
                         SEQUENCE LISTING

<160> NUMBER OF SEQ ID NOS: 5

<210> SEQ ID NO 1
<211> LENGTH: 217
<212> TYPE: PRT
<213> ORGANISM: Escherichia coli

<400> SEQUENCE: 1

Met Asn Gln Thr Leu Leu Ser Ser Phe Gly Thr Pro Phe Glu Arg Val
1               5                   10                  15

Glu Asn Ala Leu Ala Ala Leu Arg Glu Gly Arg Gly Val Met Val Leu
            20                  25                  30

Asp Asp Glu Asp Arg Glu Asn Glu Gly Asp Met Ile Phe Pro Ala Glu
        35                  40                  45

Thr Met Thr Val Glu Gln Met Ala Leu Thr Ile Arg His Gly Ser Gly
    50                  55                  60

Ile Val Cys Leu Cys Ile Thr Glu Asp Arg Arg Lys Gln Leu Asp Leu
65                  70                  75                  80

Pro Met Met Val Glu Asn Asn Thr Ser Ala Tyr Gly Thr Gly Phe Thr
                85                  90                  95

Val Thr Ile Glu Ala Ala Glu Gly Val Thr Thr Gly Val Ser Ala Ala
            100                 105                 110

Asp Arg Ile Thr Thr Val Arg Ala Ala Ile Ala Asp Gly Ala Lys Pro
        115                 120                 125

Ser Asp Leu Asn Arg Pro Gly His Val Phe Pro Leu Arg Ala Gln Ala
    130                 135                 140

Gly Gly Val Leu Thr Arg Gly Gly His Thr Glu Ala Thr Ile Asp Leu
145                 150                 155                 160

Met Thr Leu Ala Gly Phe Lys Pro Ala Gly Val Leu Cys Glu Leu Thr
                165                 170                 175

Asn Asp Asp Gly Thr Met Ala Arg Ala Pro Glu Cys Ile Glu Phe Ala
            180                 185                 190

Asn Lys His Asn Met Ala Leu Val Thr Ile Glu Asp Leu Val Ala Tyr
        195                 200                 205

Arg Gln Ala His Glu Arg Lys Ala Ser
    210                 215

<210> SEQ ID NO 2
<211> LENGTH: 324
<212> TYPE: PRT
<213> ORGANISM: Escherichia coli

<400> SEQUENCE: 2

Met Gln Tyr Asn Pro Leu Gly Lys Thr Asp Leu Arg Val Ser Arg Leu
1               5                   10                  15

Cys Leu Gly Cys Met Thr Phe Gly Glu Pro Asp Arg Gly Asn His Ala
```

```
            20                  25                  30
Trp Thr Leu Pro Glu Ser Ser Arg Pro Ile Ile Lys Arg Ala Leu
         35                  40                  45
Glu Gly Gly Ile Asn Phe Phe Asp Thr Ala Asn Ser Tyr Ser Asp Gly
     50                  55                  60
Ser Ser Glu Glu Ile Val Gly Arg Ala Leu Arg Asp Phe Ala Arg Arg
 65                  70                  75                  80
Glu Asp Val Val Ala Thr Lys Val Phe His Arg Val Gly Asp Leu
                 85                  90                  95
Pro Glu Gly Leu Ser Arg Ala Gln Ile Leu Arg Ser Ile Asp Asp Ser
             100                 105                 110
Leu Arg Arg Leu Gly Met Asp Tyr Val Asp Ile Leu Gln Ile His Arg
             115                 120                 125
Trp Asp Tyr Asn Thr Pro Ile Glu Glu Thr Leu Glu Ala Leu Asn Asp
         130                 135                 140
Val Val Lys Ala Gly Lys Ala Arg Tyr Ile Gly Ala Ser Ser Met His
145                 150                 155                 160
Ala Ser Gln Phe Ala Gln Ala Leu Glu Leu Gln Lys Gln His Gly Trp
                 165                 170                 175
Ala Gln Phe Val Ser Met Gln Asp His Tyr Asn Leu Ile Tyr Arg Glu
             180                 185                 190
Glu Glu Arg Glu Met Leu Pro Leu Cys Tyr Gln Glu Gly Val Ala Val
             195                 200                 205
Ile Pro Trp Ser Pro Leu Ala Arg Gly Arg Leu Thr Arg Pro Trp Gly
         210                 215                 220
Glu Thr Thr Ala Arg Leu Val Ser Asp Glu Val Gly Lys Asn Leu Tyr
225                 230                 235                 240
Lys Glu Ser Asp Glu Asn Asp Ala Gln Ile Ala Glu Arg Leu Thr Gly
                 245                 250                 255
Val Ser Glu Glu Leu Gly Ala Thr Arg Ala Gln Val Ala Leu Ala Trp
             260                 265                 270
Leu Leu Ser Lys Pro Gly Ile Ala Ala Pro Ile Ile Gly Thr Ser Arg
         275                 280                 285
Glu Glu Gln Leu Asp Glu Leu Leu Asn Ala Val Asp Ile Thr Leu Lys
     290                 295                 300
Pro Glu Gln Ile Ala Glu Leu Glu Thr Pro Tyr Lys Pro His Ala Val
305                 310                 315                 320
Val Gly Phe Lys

<210> SEQ ID NO 3
<211> LENGTH: 266
<212> TYPE: PRT
<213> ORGANISM: Escherichia coli

<400> SEQUENCE: 3

Met Tyr Ile Gly Ile Asp Leu Gly Thr Ser Gly Val Lys Val Ile Leu
 1               5                  10                  15
Leu Asn Glu Gln Gly Glu Val Val Ala Ser Gln Thr Glu Lys Leu Thr
             20                  25                  30
Val Ser Arg Pro His Pro Leu Trp Ser Glu Gln Asp Pro Glu Gln Trp
         35                  40                  45
Trp Gln Ala Thr Asp Arg Ala Met Lys Ala Leu Gly Asp Gln His Ser
     50                  55                  60
Leu Gln Asp Val Lys Ala Leu Gly Ile Ala Gly Gln Met His Gly Ala
```

```
                65                  70                  75                  80
Thr Leu Leu Asp Ala Gln Gln Arg Val Leu Arg Pro Ala Ile Leu Trp
                    85                  90                  95
Asn Asp Gly Arg Cys Ala Gln Glu Cys Thr Leu Leu Glu Ala Arg Val
                100                 105                 110
Pro Gln Ser Arg Val Ile Thr Gly Asn Leu Met Met Pro Gly Phe Thr
                115                 120                 125
Ala Pro Lys Leu Leu Trp Val Gln Arg His Glu Pro Glu Ile Phe Arg
                130                 135                 140
Gln Ile Asp Lys Val Leu Leu Pro Lys Asp Tyr Leu Arg Leu Arg Met
145                 150                 155                 160
Thr Gly Glu Phe Ala Ser Asp Met Ser Asp Ala Ala Gly Thr Met Trp
                    165                 170                 175
Leu Asp Val Ala Lys Arg Asp Trp Ser Asp Val Met Leu Gln Ala Cys
                180                 185                 190
Asp Leu Ser Arg Asp Gln Met Pro Ala Leu Tyr Glu Gly Ser Glu Ile
                195                 200                 205
Thr Gly Ala Leu Leu Pro Glu Val Ala Lys Ala Trp Gly Met Ala Thr
                210                 215                 220
Val Pro Val Val Ala Gly Gly Asp Asn Ala Ala Gly Ala Val Gly
225                 230                 235                 240
Val Gly Met Val Asp Ala Asn Gln Ala Met Leu Ser Leu Gly Thr Ser
                    245                 250                 255
Gly Ser Ile Leu Leu Ser Ala Lys Gly Ser
                260                 265

<210> SEQ ID NO 4
<211> LENGTH: 71
<212> TYPE: DNA
<213> ORGANISM: Artificial Sequence
<220> FEATURE:
<223> OTHER INFORMATION: Primer designed to amplify the kanamycin
      resistance marker from plasmid pDK13

<400> SEQUENCE: 4
atgagttttg atattgccaa atacccgacc ctggcactgg tcgactccac gtgtaggctg    60
gagctgcttc g                                                        71

<210> SEQ ID NO 5
<211> LENGTH: 70
<212> TYPE: DNA
<213> ORGANISM: Artificial Sequence
<220> FEATURE:
<223> OTHER INFORMATION: Primer designed to amplify the kanamycin
      resistance marker from plasmid pDK13

<400> SEQUENCE: 5
ttctacggtg accagcgctt catggctggc ggccatttcc agaattaacg atgggaatta    60
gccatggtcc                                                          70
```

US 9,637,766 B2

HOST CELLS AND METHODS FOR PRODUCING 1-DEOXYXYLULOSE 5-PHOSPHATE (DXP) AND/OR A DXP DERIVED COMPOUND

RELATED PATENT APPLICATIONS

The application claims priority as a divisional application to U.S. patent application Ser. No. 13/587,826, filed Aug. 16, 2012, which claims priority to U.S. Provisional Patent Application Ser. No. 61/524,271, filed Aug. 16, 2011, now U.S. Pat. No. 9,382,553, issued Jul. 5, 2016, which are herein incorporated by reference in their entireties.

STATEMENT OF GOVERNMENTAL SUPPORT

The invention described and claimed herein was made utilizing funds supplied by the U.S. Department of Energy under Contract No. DE-AC02-05CH11231. The government has certain rights in this invention.

FIELD OF THE INVENTION

The present invention is in the field of genetically modified host cells capable of producing 1-deoxyxylulose 5-phosphate.

BACKGROUND OF THE INVENTION

One issue associated with biosynthesis of isoprenoids is the availability of pathway precursors and competition with other central metabolic pathways. The conservation of metabolic materials (carbon) and energy is a crucial aspect of producing bioenergy in an economically competitive manner when compared to petroleum derived fuels.

As there was no known direct metabolic route from xylose to DXP, it was hoped that a synthetic pathway could be generated by identifying mutant enzymes that could catalyze novel metabolic steps. To this end, a strain of E. coli that cannot generate DXP from the normal precursors, pyruvate and glyceraldehyde-3-phosphate (G3P) is constructed, and this strain is used to select for mutants that could convert xylose to DXP.

Currently, DXP is produced by the condensation of pyruvate and glyceraldehyde-3-phosphate (G3P). This condensation results in the loss of $CO_2$ and is not an efficient method for the production of DXP. In addition, pyruvate and G3P are required for many metabolic pathways in the cell, and normally only a small fraction of these precursors is directed to DXP biosynthesis.

SUMMARY OF THE INVENTION

The present invention provides for a genetically modified host cell capable of producing 1-deoxyxylulose 5-phosphate or 1-deoxy-D-xylulose 5-phosphate (DXP) (12) comprising: (a) a mutant RibB, or functional variant thereof, or (b) a YajO, or functional variant thereof, and a XylB, or functional variant thereof. In some embodiments of the invention, the host cell in its unmodified form does not naturally have a gene which encodes or expresses 1-deoxy-d-xylulose 5-phosphate synthase (dxs gene). In some embodiments of the invention, the host cell in its unmodified form does naturally have the dxs gene, but the modified host cell has the dxs gene knocked out, or encodes a Dxs that has a reduced 1-deoxy-d-xylulose 5-phosphate synthase activity, or a reduced expression of the dxs gene, or both.

In some embodiments of the invention, the genetically modified host cell is unable or is reduced compared to the unmodified or wild-type host cell to produce IPP through the mevalonate (MEV) pathway. In some embodiments of the invention, the MEV pathway is not native to the host cell. In some embodiments of the invention, the MEV pathway is native to the host cell. In some embodiments of the invention, the MEV pathway is native to the host cell and the host cell is modified such that one or more genes of the MEV is knocked out, reduced in expression as compared to the unmodified host cell, and/or the one or more gene products of one or more genes is modified such that the corresponding one or more gene products has a reduced enzymatic activity compared to the gene product of the unmodified gene, or a combination thereof.

In some embodiments of the invention, the genetically modified host cell is further capable of producing a DXP derived compound. Such DXP derived compounds include but are not limited to 2C-methyl-D-erythritol 4-phosphate (14), compound (15), compound (16), 2C-methyl-D-erythritol 2,4-diphosphate (17), 1-hydroxy-2-methyl-2-(E)-butenyl 4-diphosphate (18), IPP (2), DMAPP (3), GPP, geraniol, farnesol, isopentanol, 3,7-dimethyloctanol, 3,7,11-trimethyldodecanol, isoprenyl alkanoate, monoterpene, sesquiterpene, diterpene, and cartenoid.

In some embodiments of the invention, the genetically modified host cell further comprises one or more genes encoding one or more enzymes capable of converting the DXP into one or more of the following compounds: 2C-methyl-D-erythritol 4-phosphate (14), compound (15), compound (16), 2C-methyl-D-erythritol 2,4-diphosphate (17), 1-hydroxy-2-methyl-2-(E)-butenyl 4-diphosphate (18), IPP (2), and DMAPP (3). The chemical structures of these compounds are shown in FIG. 4.

In some embodiments of the invention, when the genetically modified host cell is capable of producing 2C-methyl-D-erythritol 4-phosphate (14), and the host cell further comprises the gene product of the ispC (or dxr) gene.

In some embodiments of the invention, when the genetically modified host cell is capable of producing compound (15), and the host cell further comprises the gene products of the ispC and ispD (or ygbP) genes.

In some embodiments of the invention, when the genetically modified host cell is capable of producing compound (16), and the host cell further comprises the gene products of the ispC, ispD, and ispE (or ychB) genes.

In some embodiments of the invention, when the genetically modified host cell is capable of producing 2C-methyl-D-erythritol 2,4-diphosphate (17), and the host cell further comprises the gene products of the ispC, ispD, ispE, and ispF (or ygbB) genes.

In some embodiments of the invention, when the genetically modified host cell is capable of producing 1-hydroxy-2-methyl-2-(E)-butenyl 4-diphosphate (18), and the host cell further comprises the gene products of the ispC, ispD, ispE, ispF, and ispG (or gcpE) genes.

In some embodiments of the invention, when the genetically modified host cell is capable of producing IPP (2) and/or DMAPP (3), and the host cell further comprises the gene products of the ispC, ispD, ispE, ispF, ispG, and ispH (or lytB) genes.

In some embodiments of the invention, when the genetically modified host cell is capable of producing GPP and/or optionally FPP, and the host cell further comprises the gene products of the ispC, ispD, ispE, ispF, ispG, and ispH genes, and GPP synthase and/or optionally FPP synthase.

In some embodiments of the invention, when the genetically modified host cell is capable of producing isopentenol, geraniol, and/or farnesol, or isopentanol, 3,7-dimethyloctanol, and/or 3,7,11-trimethyldodecanol, or an isoprenyl alkanoate, and the host cell further comprises the gene products of the ispC, ispD, ispE, ispF, ispG, and ispH genes, and GPP synthase and/or optionally FPP synthase, and the corresponding enzymes, or functional variant thereof, described in U.S. patent application Ser. No. 12/644,531, filed Dec. 22, 2009, PCT International Application No. PCT/US2008/68756, filed Jun. 30, 2008, and U.S. Provisional Application Ser. No. 60/947,280, filed Jun. 29, 2007, hereby incorporated by reference. See FIG. 5.

In some embodiments of the invention, the genetically modified host cell is capable of producing one or more monoterpenes, sesquiterpenes, diterpenes, and/or cartenoids, and comprises the corresponding enzymes, or functional variant thereof, described in U.S. Patent Application Pub. No. 2008/0274523, hereby incorporated by reference. See FIG. 6.

In some embodiments of the invention, the genetically modified host cell comprises one or more nucleic acids encoding the gene products or enzymes described, and is capable of expressing the gene products or enzymes thereof. Each nucleic acid can be a or on a vector. The nucleic acid can also be a chromosome.

The present invention also provides for a method of producing a DXP or one or more DXP derived compounds, including but are not limited to 2C-methyl-D-erythritol 4-phosphate (14), compound (15), compound (16), 2C-methyl-D-erythritol 2,4-diphosphate (17), 1-hydroxy-2-methyl-2-(E)-butenyl 4-diphosphate (18), IPP (2), DMAPP (3), GPP, FPP, geraniol, farnesol, isopentanol, 3,7-dimethyloctanol, 3,7,11-trimethyldodecanol, isoprenyl alkanoate, monoterpene, sesquiterpene, diterpene, and/or cartenoid, in a genetically modified host cell of the present invention. The method comprises culturing the genetically modified host cell of the present invention in a medium under a suitable condition such that the culturing results in the genetically modified host cell producing the DXP or one or more DXP derived compounds, and optionally recovering the DXP or one or more DXP derived compounds from the medium, wherein the recovering step is concurrent or subsequent to the culturing step. In some embodiments of the invention, the host cell is in a medium, and providing step comprises adding or introducing the inducer to the medium.

The DXP or DXP derived compound produced using the host cell and/or method of the present invention can be useful for, or for conversion into biofuels.

The present invention provides for a more direct conversion of xylose to terpenoid compounds via a novel metabolic route that is dependent on mutations that we have identified in the ribB gene (such as amino acid substitutions S89R, T106I, and G92D).

The present invention provides for a method of synthesizing DXP or a DXP derived compound from xylose in the cell. This novel metabolic route from xylose to DXP circumvents the normal route to DXP that involves assimilation of the sugar into central metabolic pathways and generation of DXP through a step that entails competition with many other pathways for pyruvate and G3P. In some embodiments of the invention, the invention is capable of converting 20% of xylose-derived carbon into DXP derived compounds, such as terpenoid products.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1A:
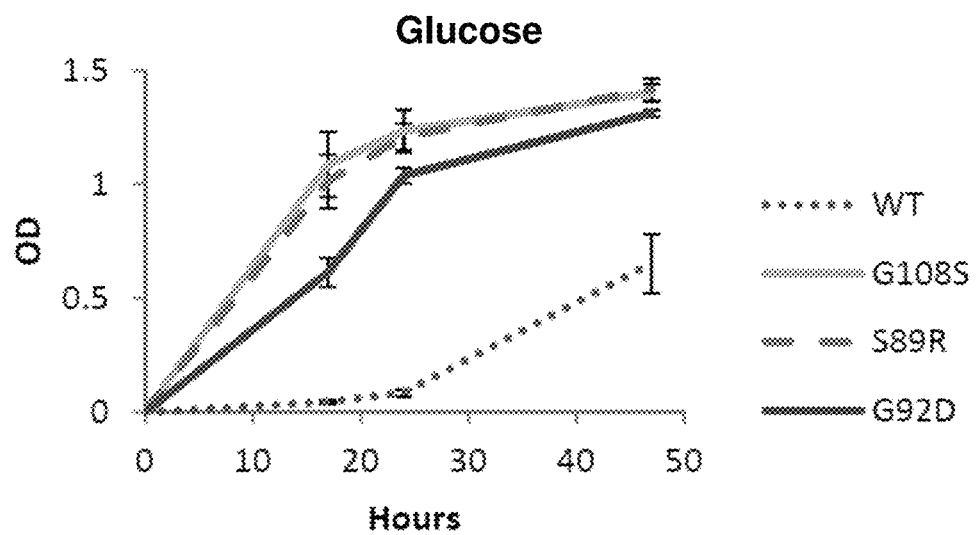
FIG. 1A shows the growth of *E. coli* Δdxs harboring plasmids containing either the wild type ribB gene (WT), or a ribB mutant (G108S, S89R, G92D). All strains also contain the plasmid pMBI, which contains the bottom half of the mevalonate pathway (Martin V J, Pitera D J, Withers S T, Newman J D, Keasling J D, *Nat Biotechnol*. 2003 July; 21(7):796-802), and enables growth of the *E. coli* Δdxs strain in the presence of mevalonate. In the absence of mevalonate, expression of the native ribB gene enables a low level of growth on glucose and xylose, while the ribB mutants enable growth rates similar to those observed with mevalonate supplementation.
Figure 1B:
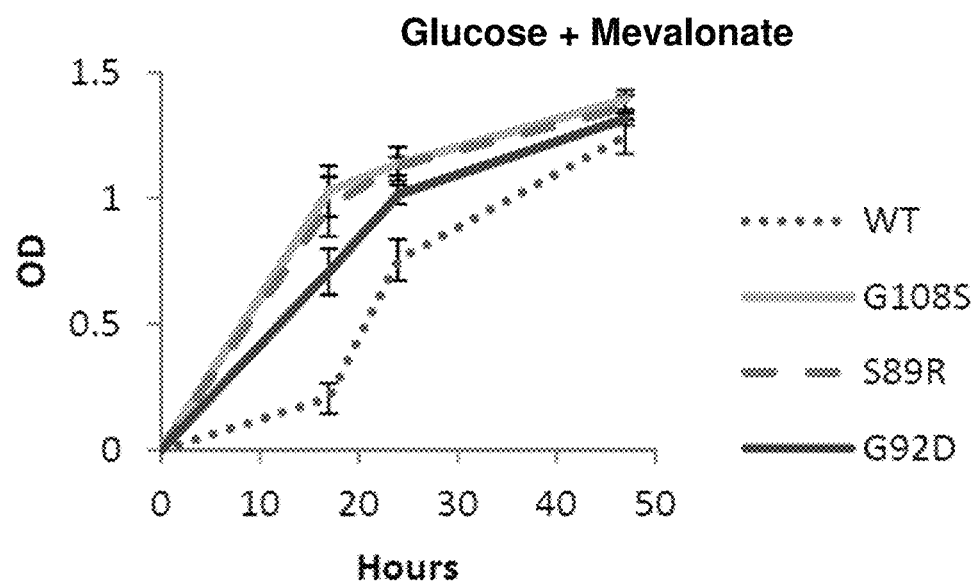
FIG. 1B shows the growth of *E. coli* Δdxs harboring plasmids containing either the wild type ribB gene (WT), or a ribB mutant (G108S, S89R, G92D). All strains also contain the plasmid pMBI, which contains the bottom half of the mevalonate pathway (Martin et al., 2003), and enables growth of the *E. coli* Δdxs strain in the presence of mevalonate. In the absence of mevalonate, expression of the native ribB gene enables a low level of growth on glucose and xylose, while the ribB mutants enable growth rates similar to those observed with mevalonate supplementation.
Figure 1C:
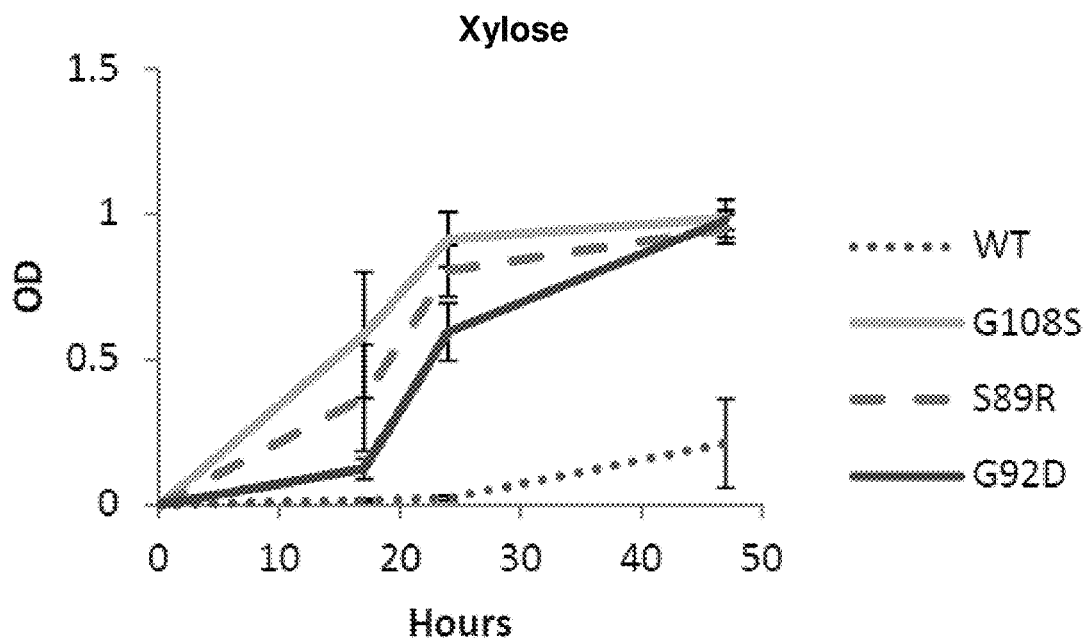
FIG. 1C shows the growth of *E. coli* Δdxs harboring plasmids containing either the wild type ribB gene (WT), or a ribB mutant (G108S, S89R, G92D). All strains also contain the plasmid pMBI, which contains the bottom half of the mevalonate pathway (Martin et al., 2003), and enables growth of the *E. coli* Δdxs strain in the presence of mevalonate. In the absence of mevalonate, expression of the native ribB gene enables a low level of growth on glucose and xylose, while the ribB mutants enable growth rates similar to those observed with mevalonate supplementation.
Figure 1D:
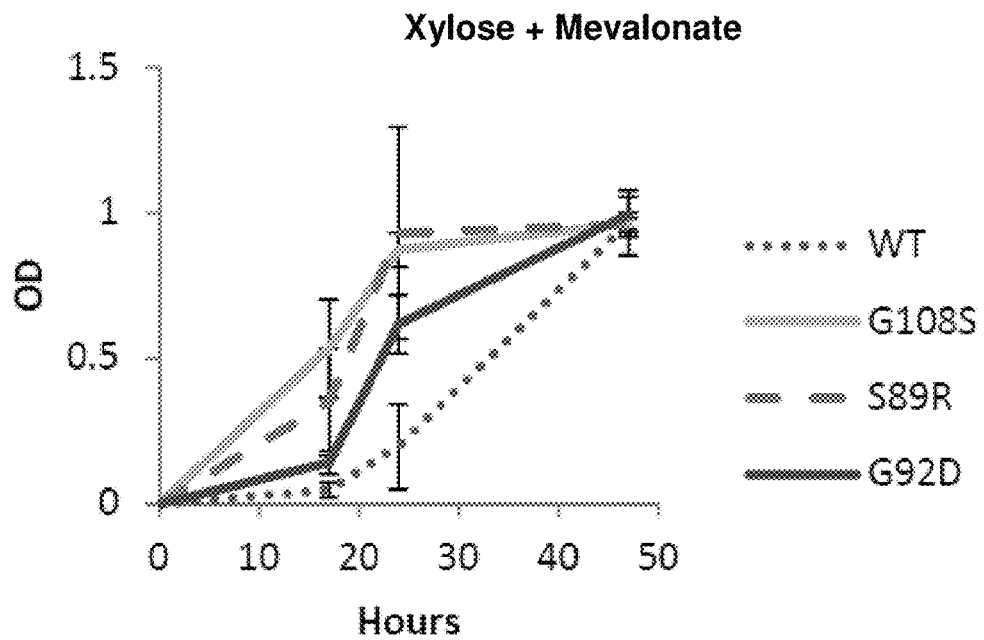
FIG. 1D shows the growth of *E. coli* Δdxs harboring plasmids containing either the wild type ribB gene (WT), or a ribB mutant (G108S, S89R, G92D). All strains also contain the plasmid pMBI, which contains the bottom half of the mevalonate pathway (Martin et al., 2003), and enables growth of the *E. coli* Δdxs strain in the presence of mevalonate. In the absence of mevalonate, expression of the native ribB gene enables a low level of growth on glucose and xylose, while the ribB mutants enable growth rates similar to those observed with mevalonate supplementation.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

The term "functional variant" describes an enzyme that has a polypeptide sequence that is at least 70%, 75%, 80%, 85%, 90%, 95% or 99% identical to any one of the enzymes described herein. The "functional variant" enzyme may retain amino acids residues that are recognized as conserved for the enzyme, and may have non-conserved amino acid residues substituted or found to be of a different amino acid, or amino acid(s) inserted or deleted, but which does not affect or has insignificant effect its enzymatic activity, as compared to the enzyme described herein. The "functional variant" enzyme has an enzymatic activity that is identical or essentially identical to the biological activity of the regulator or enzyme described herein. The "functional variant" enzyme may be found in nature, i.e. naturally occurring, or be an engineered mutant thereof.

The term "plant" includes reference to whole plants, plant organs (for example, leaves, stems, roots, etc.), seeds, and plant cells and progeny of same. Plant cell, as used herein includes, without limitation, seeds, suspension cultures, embryos, meristematic regions, callus tissue, leaves roots shoots, gametophytes, sporophytes, pollen, and microspores. The class of plants that can be used in the methods of the present invention is generally as broad as the class of higher plants amenable to transformation techniques, including both monocotyledonous and dicotyledonous plants.

These and other objects, advantages, and features of the invention will become apparent to those persons skilled in the art upon reading the details of the invention as more fully described below.

The *E. coli* ribB gene encodes the RibB protein which is the 3,4-dihydroxy-2-butanone 4-phosphate synthase, and has following amino acid sequence:

```
                                                            (SEQ ID NO: 1)
  1 mnqtllssfg tpfervenal aalregrgvm vlddedrene gdmifpaetm tveqmaltir 61 hgsgivclci tedrrkqldl pmmvenntsa ygtgftvtie aaegvttgvs aadrittvra 121 aiadgakpsd lnrpghvfpl raqaggvltr gghteatidl mtlagfkpag vlceltnddg 181 tmarapecie fankhnmalv tiedlvayrq aherkas
```

The RibB mutant comprises a polypeptide comprising an amino acid sequence of wild-type RibB, such as *E. coli* RibB, or equal to or more than 70%, 80%, 85%, 90%, 95%, or 99% sequence identity with wild-type RibB, but with one or more mutation, such as one or more amino acid substitution, deletion, and/or insertion, such that the RibB mutant comprises the enzymatic activity of catalyzing xylulose 5-phoshpate and/or ribulose-5-phospate to DXP. In some embodiments of the invention, the RibB comprises one or more amino acid substitutions within the region of between amino acid positions 87 and 128 of the *E. coli* RibB, and/or within the region of between amino acid positions 169-196 of the *E. coli* RibB. In some embodiments of the invention, the RibB comprises one or more of the following amino acid substitutions: G108S, T88I, S89R, V109I, M182I, G92D, and T106I. In some embodiments of the invention, the RibB comprises the following amino acid substitutions: G108S and T88I, G108S and S89R, G108S and V109I, G108S and M182I, G108S and G92D, G108S and T106I, T88I and S89R, T88I and V109I, T88I and M182I, T88I and G92D, T88I and T106I, S89R and V109I, S89R and M182I, S89R and G92D, S89R and T106I, V109I and M182I, V109I and G92D, V109I and T106I, M182I and G92D, M182I and T106I, and G92D and T106I. In some embodiments of the invention, the RibB comprises three, four, five, six, or all of the following amino acid substitutions: G108S, T88I, S89R, V109I, M182I, G92D, and T106I.

The *E. coli* yajO gene encodes the YajO protein which has following amino acid sequence:

```
                                                            (SEQ ID NO: 2)
  1 mqynplgktd lrvsrlclgc mtfgepdrgn hawtlpeess rpiikraleg ginffdtans 61 ysdgsseeiv gralrdfarr edvvvatkvf hrvgdlpegl sraqilrsid dslrrlgmdy 121 vdilqihrwd yntpieetle alndvvkagk aryigassmh asqfaqalel qkqhgwaqfv 181 smqdhynliy reeeremlpl cyqegvavip wsplargrlt rpwgettarl vsdevgknly 241 kesdendaqi aerltgvsee lgatraqval awllskpgia apiigtsree qldellnavd 301 itlkpeqiae letpykphav vgfk
```

The *E. coli* xylB gene encodes the xylB protein which has following amino acid sequence:

```
                                                            (SEQ ID NO: 3)
  1 myigidlgts gvkvillneq gevvasqtek ltvsrphplw seqdpeqwwq atdramkalg 61 dqhslqdvka lgiagqmhga tlldaqqrvl rpailwndgr caqectllea rvpqsrvitg 121 nlmmpgftap kllwvqrhep eifrqidkvl lpkdylrlrm tgefasdmsd aagtmwldva 181 krdwsdvmlq acdlsrdqmp alyegseitg allpevakaw gmatvpvvag ggdnaagavg 241 vgmvdanqam lslgtsgsil lsakgs
```

YajO enables converts xylulose to 1-deoxyxylulose (DX), and that the metabolic adaptation that takes place is an upregulation of xylB gene expression. XylB is able to phosphorylate DX to produce DXP. When both YajO and XylB are present, they can convert xylulose to DXP. YajO converts xylulose to DX, and XylB converts the DX to DXP.

In some embodiments of the invention, the host cell comprises an open reading frame (ORF) encoding a RibB mutant, or YajO and XylB, or a functional variant thereof, operably linked to a promoter. In some embodiments of the invention, the promoter can a heterologous promoter, either heterologous to the ORF or the host cell. In some embodiments of the invention, the heterologous promoter is a constitutive or inducible promoter. In some embodiments of the invention, the inducible promoter can be any inducible promoter that increases or elevates expression when an inducer is present in the host cell or environment of the host cell. In some embodiments of the invention, the inducer can be introduced to the host cell by introducing the inducer to the environment of the host cell, i.e. the inducer can enter into the host cell. In some embodiments of the invention, the ORF is operably linked to an inducible promoter, and one skilled in the art is capable of adjusting the amount of inducer present in order to determine the amount of inducer in the environment of the cell in order to obtain the optimum or maximum production of DXP or a DXP derived compound.

In some embodiments of the invention, the host cell comprises a plurality of the ORF encoding a enzyme or mutant thereof described herein, or a functional variant thereof. The ORFs of the plurality of ORF can each independently have a nucleotide sequence different from another ORF. For example, every ORF within the host cell can have a different nucleotide sequence and/or encode a YajO, or a functional variant thereof, with a different amino acid sequence, or every ORF with the host cell can have a different nucleotide sequence and each ORF encodes a YajO, or a functional variant thereof, with the same amino acid sequence, or every ORF with the host cell can have the same nucleotide sequence. In some embodiments of the invention, an ORF encoding any enzyme described herein, or a functional variant thereof, can be optimized for expression of that particular amino acid sequence. In some embodiments of the invention, an ORF has a naturally occurring nucleotide sequence. In some embodiments of the invention, an ORF encodes an enzyme described herein with a naturally occurring amino acid sequence.

In some embodiments of the invention, the host cell comprises one or more ORFs encoding proteins, or functional variants thereof, involved in the production of DXP or a DXP derived compound.

An ORF can stably reside on the chromosome of the host cell. An ORF can reside on a vector. The vector can be capable of stable maintenance with the host cell. The host cell can comprise one or more ORFs residing on the chromosome of the host cell, one or more vectors comprising one or more ORFs, or both.

In some embodiments of the invention, the host cell is capable of producing DXP or one or more DXP derived compounds from a conversion equal to or more than about 10, 20, 30, 40, 50, 60, 70, or 80% of the xylose provided to the host cell. In some embodiments of the invention, the host cell is capable of producing DXP or one or more DXP derived compounds from a conversion ranging from about 10, 20, 30, or 40% to about 50, 60, 70, or 80% of the xylose source provided to the host cell. In some embodiments of the invention, the percent conversion to a DXP or one or more DXP derived compounds from the xylose provided to the host cell is under conditions comprising growth in a minimal media comprising 2% xylose and three days of incubation at 37° C.

The nucleic acid constructs of the present invention comprise nucleic acid sequences encoding one or more of the subject regulator or enzyme. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject regulator or enzyme are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. An example includes lactose promoters (LacI repressor protein changes conformation when contacted with lactose, thereby preventing the LacI repressor protein from binding to the operator). Another example is the tac promoter. (See deBoer et al. (1983) *Proc. Natl. Acad. Sci. USA*, 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell is transformed with at least one expression vector. When only a single expression vector is used (without the addition of an intermediate), the vector will contain all of the nucleic acid sequences necessary.

As the host cell grows and/or multiplies, expression of the enzymes for producing the DXP and/or DXP derived compound is effected. Once expressed, the enzymes catalyze the steps necessary for carrying out the steps of DXP and/or DXP derived compound production. Any means for recovering the DXP and/or DXP derived compound from the host cell may be used. For example, the host cell may be harvested and subjected to hypotonic conditions, thereby lysing the cells. The lysate may then be centrifuged and the supernatant subjected to high performance liquid chromatography (HPLC) or gas chromatography (GC). Once the DXP and/or DXP derived compound is recovered, modification, as desired, may be carried out on the DXP and/or DXP derived compound.

Host Cells

The host cells of the present invention are genetically modified in that heterologous nucleic acid have been introduced into the host cells, and as such the genetically modified host cells do not occur in nature. The suitable host cell is one capable of expressing a nucleic acid construct encoding one or more regulators or enzymes described herein. The gene(s) encoding the regulator(s) or enzymes (s) may be heterogous to the host cell or the gene may be native to the host cell but is operatively linked to a heterologous promoter and one or more control regions which result in a higher expression of the gene in the host cell.

The regulators or enzymes can be native or heterologous to the host cell. Where the enzyme is native to the host cell, the host cell is genetically modified to modulate expression of the regulators or enzymes. This modification can involve the modification of the chromosomal gene encoding the regulators or enzymes in the host cell or a nucleic acid construct encoding the gene of the regulators or enzymes is introduced into the host cell. One of the effects of the modification is the expression of the regulators or enzymes is modulated in the host cell, such as the increased expression of the regulators or enzymes in the host cell as compared to the expression of the enzyme in an unmodified host cell.

In some embodiments of the invention, the host cell is a microorganism from the Enterobacteriaceae family. In some embodiments of the invention, the host cell is a Gram negative *bacterium*. In some embodiments of the invention, the host cell is a microorganism from the *Escherichia, Salmonella, Vibrio, Pasteurella, Haemophilus,* or *Pseudomonas* genus. In some embodiments of the invention, the host cell is a microorganism from the species *Escherichia coli, Salmonella enterica, Vibrio cholerae, Pasteurella multocida, Haemophilus influenza,* or *Pseudomonas aeruginosa*.

Any suitable host cell may be used in the practice of the present invention. In one embodiment, the host cell is a genetically modified host microorganism in which nucleic acid molecules have been inserted, deleted or modified (i.e., mutated; e.g., by insertion, deletion, substitution, and/or inversion of nucleotides), to either produce the desired isoprenoid compound or isoprenoid derivative, or effect an increased yield of the desired isoprenoid compound or isoprenoid derivative. In another embodiment, the host cell is capable of being grown in liquid growth medium. In contrast, a "control cell" is an alternative subject or sample used in an experiment for comparison purpose, and is typically a parental cell that does not contain the modification(s) made to a corresponding host cell.

Illustrative examples of suitable host cells include any archae, prokaryotic, or eukaryotic cell. Examples of an archae cell include, but are not limited to those belonging to the genera: *Aeropyrum, Archaeglobus, Halobacterium, Methanococcus, Methanobacterium, Pyrococcus, Sulfolobus,* and *Thermoplasma*. Illustrative examples of archae strains include but are not limited to: *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum, Thermoplasma volcanium*.

Examples of a procaryotic cell include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus,* and *Zymomonas*.

Illustrative examples of prokaryotic bacterial strains include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus,* and the like.

In general, if a bacterial host cell is used, a non-pathogenic strain is preferred. Illustrative examples of non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum,* and the like.

Examples of eukaryotic cells include but are not limited to fungal cells and plant cells. Examples of fungal cell include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces, Trichoderma* and *Xanthophyllomyces* (formerly *Phaffia*).

The plants cells can be isolated plant cells or part of a seed, plant tissue, plant part or a whole plant comprising a cell of the present invention. In some embodiments, the plant part is a leaf, leaf stalk, stem, root, or a combination thereof. In some embodiments, the whole plant includes, but is not limited to, a germinating seed. The plant cell can be a monoct or a dicot. In some embodiments, the monocot is a grass. In some embodiments the plant is a woody plant such as Eucalyptus, cottonwood, alder, Douglas fir, Hemlock, pine or spruce. In some embodiments, the plant is a leguminous plant, including, but not limited to, alfalfa, clover, lucerne, birdsfoot trefoil, Stylosanthes, Lotononis bainessii, and sainfoin. In some embodiments, the plant is a forage grass, including, but not limited to, bahiagrass, bermudagrass, dallisgrass, pangolagrass, big bluestem, indiangrass, switchgrass, smooth bromegrass, orchardgrass, timothy, Kentucky bluegrass or tall fescue.

Illustrative examples of eukaryotic strains include but are not limited to: *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, S accaromyces bayanus, Saccaromyces boulardi, Saccharomyces cerevisiae, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Trichoderma reesei* and *Xanthophyllomyces dendrorhous* (formerly *Phaffia rhodozyma*).

In general, if a eukaryotic cell is used, a non-pathogenic strain is preferred. Illustrative examples of non-pathogenic strains include but are not limited to: *Fusarium graminearum, Fusarium venenatum, Pichia pastoris, Saccaromyces boulardi*, and *Saccaromyces cerevisiae*.

In addition, certain strains have been designated by the Food and Drug Administration as GRAS or Generally Regarded As Safe. These strains include: *Bacillus subtilis, Lactibacillus acidophilus, Lactobacillus helveticus,* and *Saccharomyces cerevisiae*.

The present invention is applicable to organisms that are capable of using the DXP pathway (bacteria such as *E. coli*, and plants). The present invention is also applicable to isoprenoid production in organisms not naturally capable of using DXP, such as yeast. One embodiment of the invention, is the production of vitamins B1 and B6 in a genetically modified yeast host cell which is modified to produce DXP (Fung P K, Krushkal J, Weathers P J. *Chem Biodivers.* 2010 May; 7(5):1098-110; hereby incorporated by reference).

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Two novel pathways from sugars such as xylose or glucose to the DXP pathway intermediate 1-deoxyxylulose 5-phosphate (DXP) are identified. They are: (1) mutants of the native *E. coli* ribB gene that can catalyze the conversion of xylulose 5-phoshpate or ribulose 5-phospate to DXP, and (2) overexpression of the native *E. coli* genes yajO and xylB that can together catalyze the conversion of xylulose to DXP.

Both of these pathways enable growth of an *E. coli* mutant (Δdxs) that lacks the native enzyme (Dxs) for making DXP. The *E. coli* Δdxs mutant is unable to grow under normal laboratory conditions, as *E. coli* is dependent on isoprenoid biosynthesis through the DXP pathway to synthesize essential metabolites such as quinones. (We are able to construct and grow this mutant by first transforming *E. coli* with the plasmid pMBI, which contains the bottom half of the mevalonate pathway (Martin et al., 2003). The pMBI plasmid enables growth of the *E. coli* Δdxs strain in the presence of mevalonate). The following describes the relative growth rates that are enabled by the two novel DXP biosynthetic pathways:

(1) ribB. *E. coli* contains a copy of the ribB gene on its chromosome, but this does not enable growth of *E. coli* in the absence of dxs. We have found that overexpression of the ribB gene on a plasmid enables very slow growth of the *E. coli* Δdxs mutant (FIGS. 1A to 1D). We have identified several ribB mutants that enable growth of the *E. coli* Δdxs strain at much faster rates, using either xylose or glucose as sole carbon source (FIGS. 1A to 1D). The ribB mutations identified so far confer the following amino acid mutations to the native *E. coli* RibB protein: G108S, T88I, S89R, V109I, M182I, G92D, and T106I. Other mutations should be possible that allow growth of an *E. coli* Δdxs mutant, and they likely reside between amino acid positions 87 and 128 in the *E. coli* RibB protein, and the region between amino acid positions 169-196. Since the native RibB protein catalyzes a reaction in which ribulose-5-phosphate as substrate, RibB mutants can convert either xylulose 5-phoshpate or ribulose 5-phospate to DXP.

Figure 2:
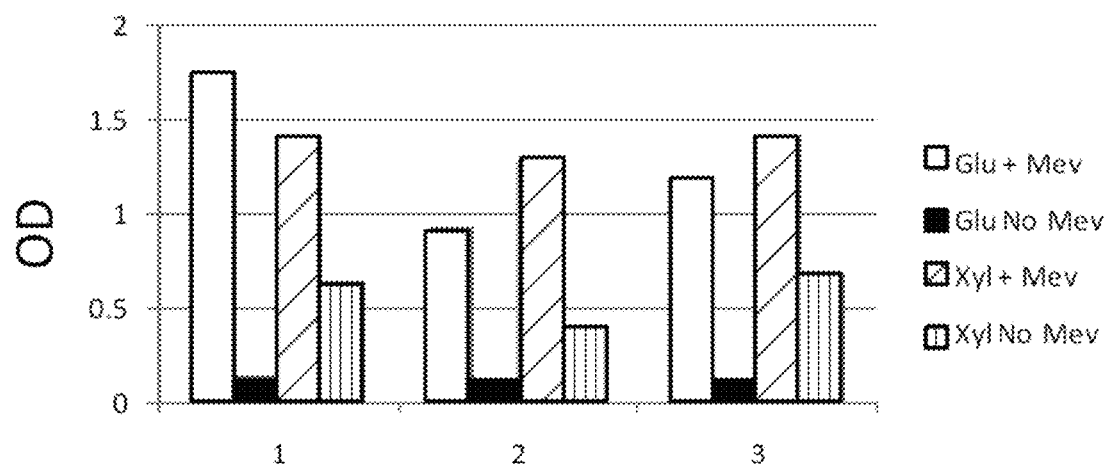
FIG. 2 shows the growth of *E. coli* Δdxs harboring a plasmid enabling overexpression of the yajO gene. All strains contain the plasmid pMBI, which contains the bottom half of the mevalonate pathway (Martin, 2003), and enables growth of the *E. coli* Δdxs strain in the presence of mevalonate. Three independent yajO transformants are shown to be able to grow in the absence of mevalonate, when using xylose as sole carbon source. Co-expression of the XylB conferred further improvements in growth (data not shown; we are currently generating data to show a comparison between YajO and YajO+XylB).

(2) yajO and xylB. We found that overexpression of the native *E. coli* gene yajO enables slow growth of the *E. coli* Δdxs mutant using xylose as sole carbon source (FIG. 2), and that growth rate improves following a period of metabolic adaptation. YajO enables converts xylulose to 1-deoxyxylulose (DX), and that the metabolic adaptation that takes place is an upregulation of xylB gene expression. XylB, which normally converts xylulose to xylulose 5-phosphate, is also known to be able to phosphorylate DX to make DXP (Wungsintaweekul J, Herz S, Hecht S, Eisenreich W, Feicht R, Rohdich F, Bacher A, Zenk M H, Eur J Biochem. 2001 January; 268(2):310-6; hereby incorporated by reference). To date, no enzyme has been reported to synthesize DX.) Both yajO and xylB are overexpressed on a plasmid, and the growth rate of the *E. coli* Δdxs mutant is improved relative to strains expressing yajO alone. Furthermore, by increasing the strength of the ribosome binding site on the yajO-xylB plasmid, there is a further improvement in growth.

A comparison of FIGS. 1A to 1D and 2 shows that the two pathways differ in their phenotypes. Expression of RibB mutants enables growth in both glucose and xylose, reflecting the fact that the likely RibB substrate (xylulose 5-phoshpate or ribulose 5-phosphate) can be made from any carbon source. On the other hand, YajO enables growth in xylose but not glucose, reflecting the fact that the likely YajO substrate (xylulose) is generated through xylose metabolism but not glucose metabolism. These different routes may have different advantages in enabling an increase in flux to DXP. The ribB route appears to be more efficient, and can divert any carbon source to DXP. The YajO route may be able to efficiently capture carbon from the xylose catabolic pathway (as xylulose), before it enters central metabolism (into the pentose phosphate pathway as xylulose 5-phosphate).

Production of Isoprenoids Using These Novel Pathways.

Figure 3A:
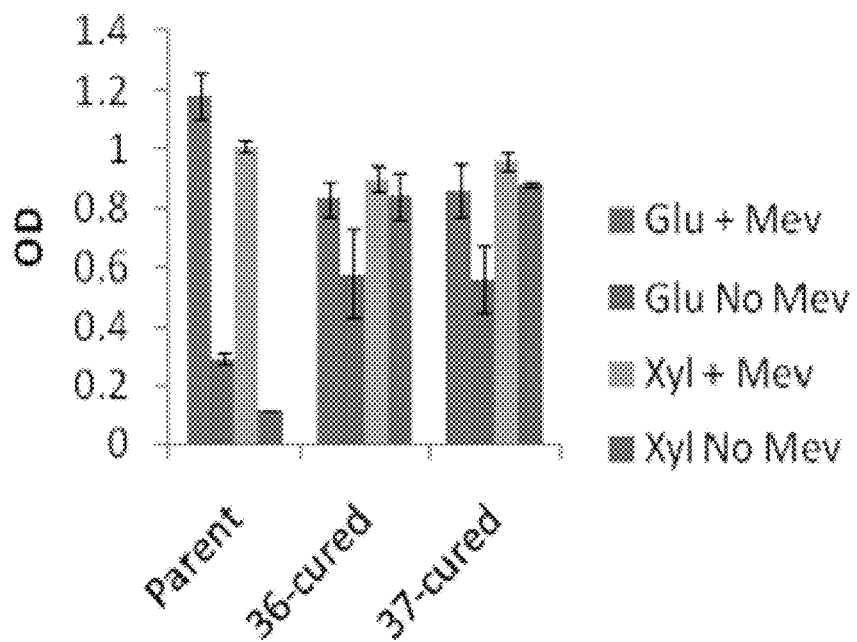
FIG. 3A shows the growth of the *E. coli* Δdxs parent strain, and corresponding RibB G92D mutant strains (36-cured and 37-cured), grown on either glucose or xylose as sole carbon-source. All strains contain the plasmid pMBI, which contains the bottom half of the mevalonate pathway and enables growth of the *E. coli* Δdxs strain in the presence of mevalonate, and also the pADS plasmids which harbors the amorphadiene synthase gene from *Artemisia annua* (Martin et al., 2003).
Figure 3B:
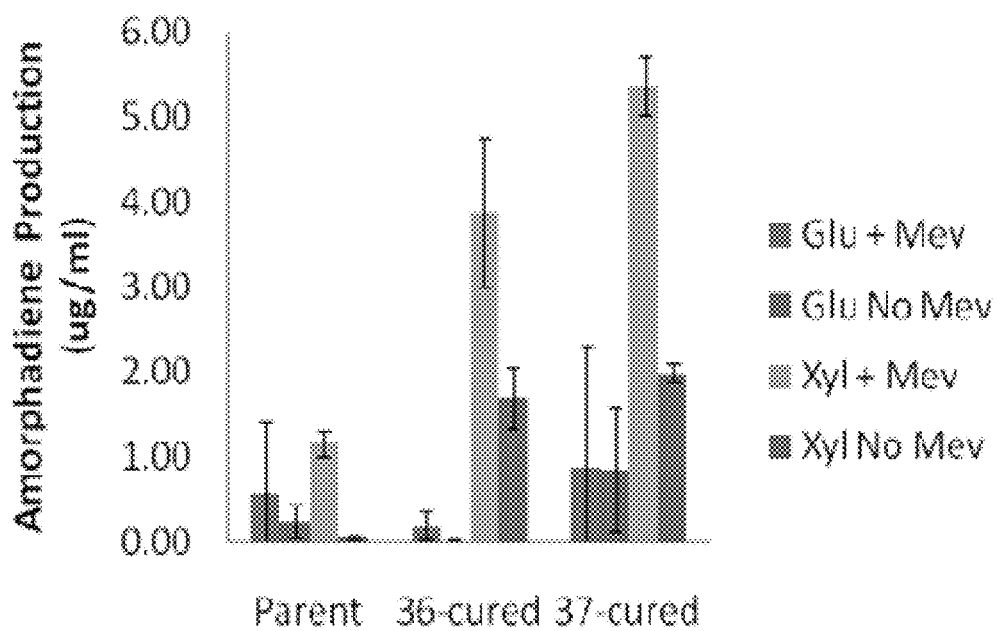
FIG. 3B shows amorphadiene production in the *E. coli* Δdxs parent strain, and corresponding RibB G92D mutant strains (36-cured and 37-cured), grown on either glucose or xylose as sole carbon-source. All strains contain the plasmid pMBI, which contains the bottom half of the mevalonate pathway and enables growth of the *E. coli* Δdxs strain in the presence of mevalonate, and also the pADS plasmids which harbors the amorphadiene synthase gene from *Artemisia annua* (Martin et al., 2003).
Figure 4:
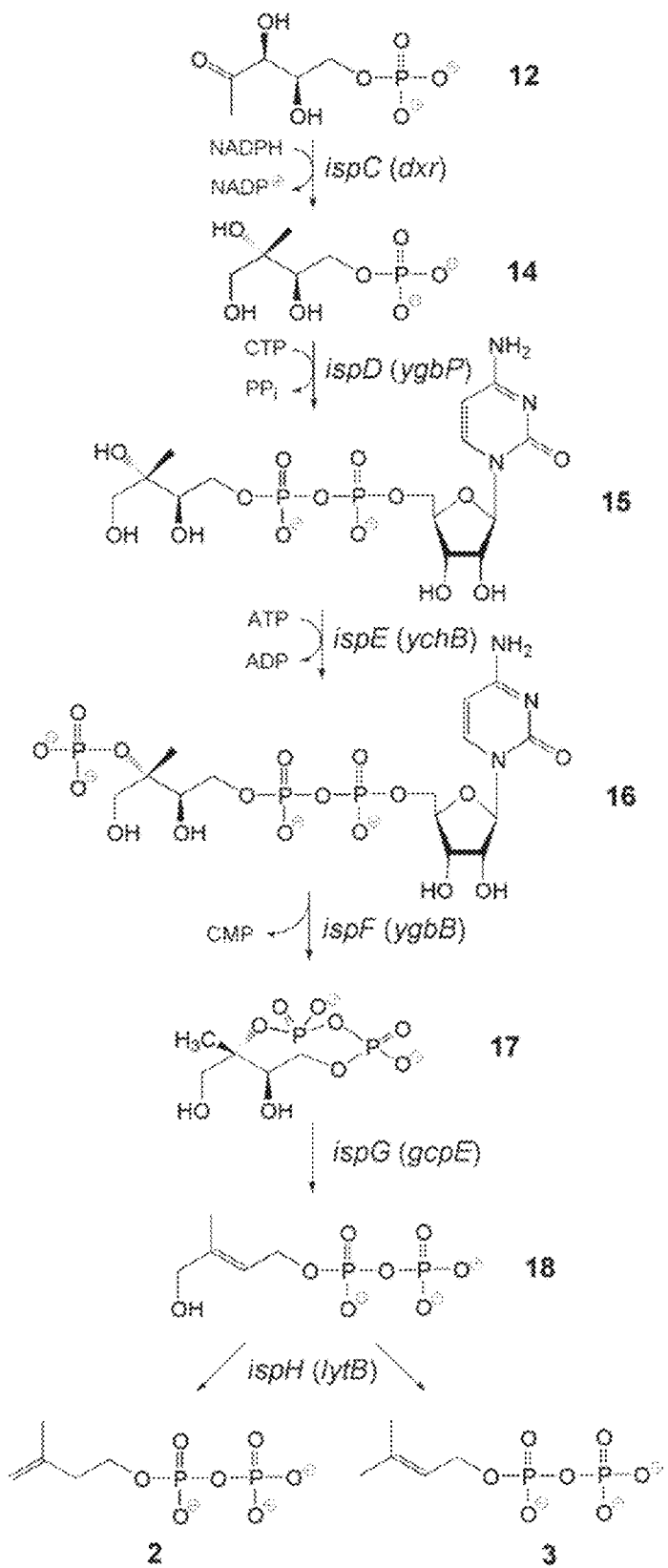
FIG. 4 shows the deoxyxylulose phosphate pathway of IPP (2) and DMAPP (3) biosynthesis. 1-deoxy-D-xylulose 5-phosphate (12) (DXP) obtained by condensation of pyruvate undergoes a rearrangement coupled to a reduction step. The resulting 2C-methyl-D-erythritol 4-phosphate (14) is converted into its cyclic diphosphate (17) by the sequential action of three enzyme activities. 2C-Methyl-D-erythritol 2,4-diphosphate (17) is transformed into IPP (2) and DMAPP (3) via 1-hydroxy-2-methyl-2-(E)-butenyl 4-diphosphate (18). These reaction steps are described in more detail in Eisenreich et al., *Cell Mol Life Sci.* 61 (2004) 14011426, hereby incorporated by reference.
Figure 5:
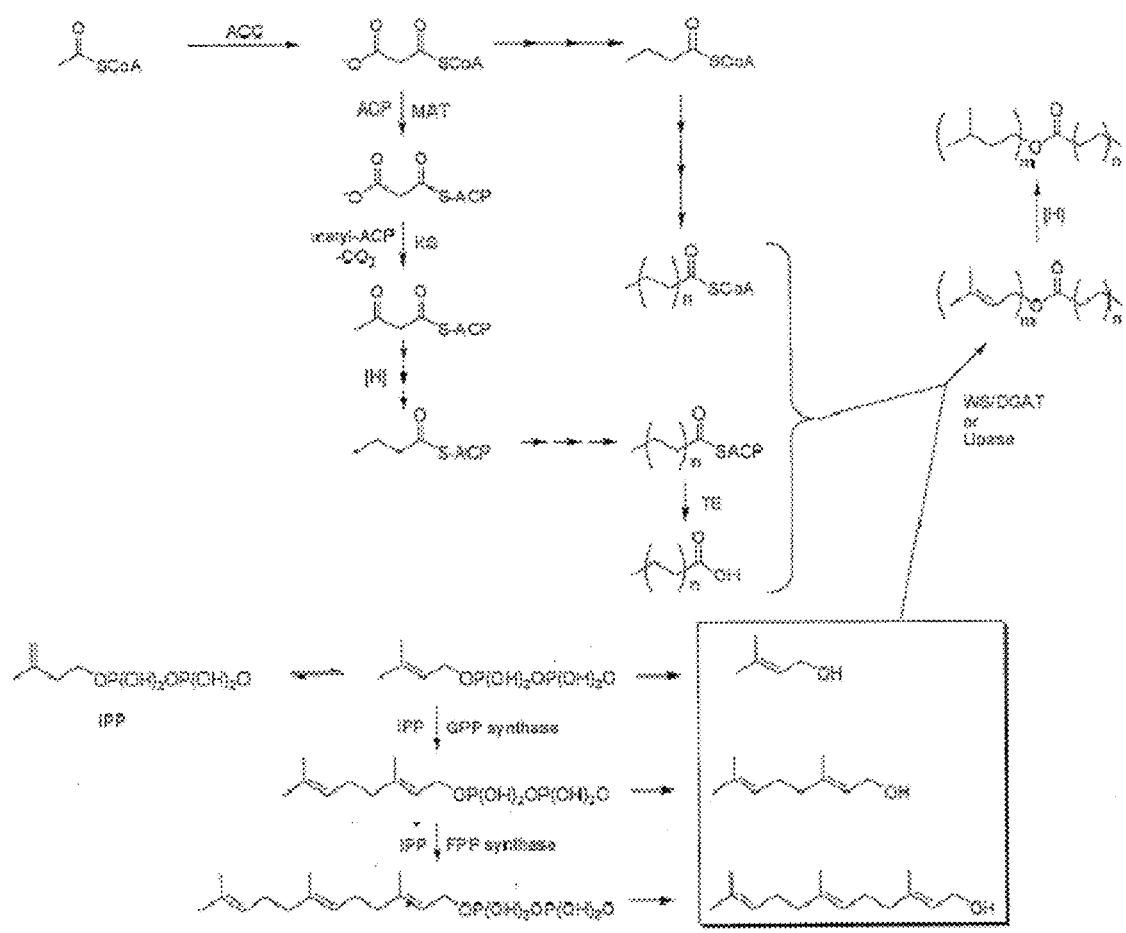
FIG. 5 shows the biosynthesis of isoprenyl alkanoates. Terpene biosynthetic pathway will generate isopentenol, geraniol, and farnesol. Various fatty acid synthetic pathways will generate a range of fatty acids with different but controllable length. Wax ester synthase-/acyl-coenzyme A: diacylglycerol acyltransferase (WS/DGAT) or lipases catalyze the esterification between terpenols and fatty acids, and the ester products are hydrogenated via chemical process.
Figure 6:
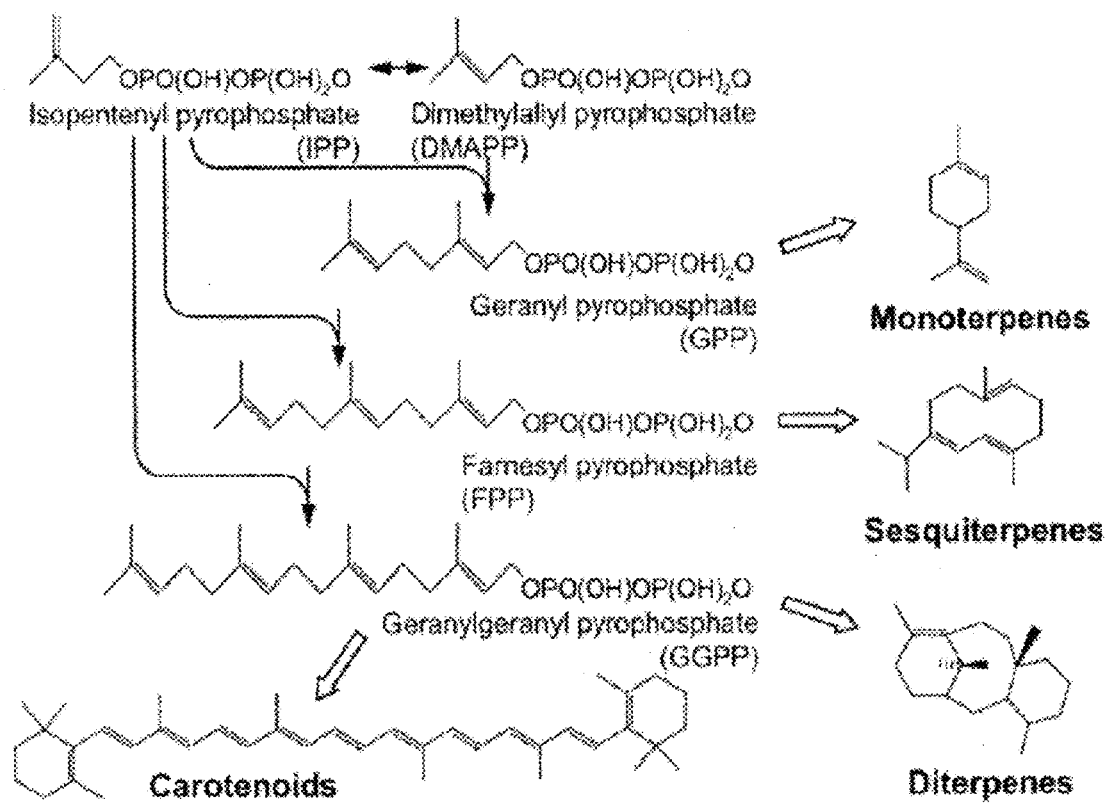
FIG. 6 shows a schematic representation of the conversion of IPP and di ethylallyl pyrophosphate (DMAPP) to geranyl pyrophosphate (GPP), farnesyl pyrophosphate (FPP), and geranyl pyrophosphate (GGPP), and the synthesis of various isoprenoids.

In order to demonstrate that these novel pathways can increase flux to DXP, and hence improve yields of isoprenoid-based molecules (or DXP-derived vitamins), sesquiterpene production is tested in the presence of these pathways. There is a benefit in expressing a ribB mutant to enhance isoprenoid production. Two mutants (36-cured and 37-cured) have genomic ribB (G92D) mutations and produce significantly more amorphadiene than the corresponding parent strain (*E. coli* Δdxs). The parent strain cannot grow in the absence of mevalonate, and produces very little amorphadiene even in the presence of mevalonate. Amorphadiene titers in the RibB G92D mutant strains is particularly high when xylose is used as a sole carbon source (FIGS. 3A to 3B).

Isoprenoid titers should improve when: (1) the best ribB mutant (G108S) is expressed on a plasmid; and (2) it is combine with an engineered DXP pathway.

Materials and Methods.

Development of a selection for novel routes to DXP. A selection for alternative routes to DXP was developed in *Escherichia coli* by knocking out the native gene responsible for DXP biosynthesis, dxs. Since *E. coli* requires isoprenoids for growth, we provided an alternative mechanism for isoprenoid biosynthesis—the lower half of the mevalonate pathway. To achieve this, *E. coli* MG1655 was transformed with the plasmid pMBI (Martin et al., 2003) that harbors four genes (ERG12, mevalonate kinase; ERG8, phosphomevaloante kinase; MVD1, mevalonate pyrophosphate decarboxylase; and idi, IPP isomerase) enabling biosynthesis of the isoprenoid precursors IPP and DMAPP when mevalonate is supplied exogenously to cells. Following transformation with pMBI, the dxs gene was knocked out by replacement with a kanamycin marker cassette in the presence of γ Red recombinase (Datsenko K A, Wanner B L, Proc Natl Acad Sci USA. 2000 Jun. 6; 97(12):6640-5; hereby incorporated by reference). Briefly, the kanamycin marker cassette was amplified by PCR from plasmid pDK13 (Datsenko and Wanner, 2000) using primers that have 50 nucleotides at their 5' ends with homology to the dxs gene (underlined below).

```
Jim031510-dxsKO-f:
atgagttttgatattgccaaatacccgaccctggcactggtcgactc cacgtgtaggctggagctgcttcg (SEQ ID NO: 4)

Jim031510-dxsKO-r:
ttctacggtgaccagcgcttcatggctggcggccatttccagaatta acgatgggaattagccatggtcc (SEQ ID NO: 5)
```

The *E. coli* MG1655 pMBI strain was transformed with this PCR product and the plasmid pKD46, which harbors the gene for γ Red recombinase (Datsenko and Wanner, 2000). Following selection on LB-kanamycin agar plates, deletion of dxs was confirmed by several diagnostic PCRs, and loss of the temperature-sensitive pDK46 plasmid was facilitated by growth at 37° C.

Use of Selective Pressure to Identify Novel Mutants.

The parent strain used for this work is referred to as Δdxs pMBI, and comprises *E. coli* MG1655 with a deletion of dxs, and harboring the pMBI plasmid, which enables isoprenoid production from exogenously-supplied mevalonate. This strain cannot grow in the absence of mevalonate, since it cannot utilize the endogenous DXP pathway for isoprenoid production. Continuous subculturing of this strain was carried out in EZ-rich medium (Teknova, Hollister, Calif., USA) with xylose as carbon source. Selective pressure was applied by reducing the concentration of mevalonate from 1.0 mM to 0.1 mM, thus limiting growth by restricting isoprenoid biosynthesis through the mevalonate pathway. At regular intervals during this process, aliquots from the 0.1 mM mevalonate subcultures were plated onto EZ-rich-xylose agar plates containing no mevalonate. Colonies that emerged in the absence of mevalonate were further tested for growth in liquid culture in the absence of mevalonate and the most promising strains were stored for further analysis.

Genome Sequencing of Mevalonate-Independent ΔDxs pMBI Strains.

Strains that were isolated under selective pressure and found to grow well in the absence of mevalonate were submitted to the Joint Genome Institute (JGI) for genome sequencing, using the parent Δdxs pMBI strain as a reference. The most promising strains were all found to have single nucleotide mutations in the ribB gene, each translating into amino acid changes in the predicted RibB protein sequence. Three of the strains had RibB G92D mutations, three of them had RibB S89R mutations, and two of them had RibB T106I mutations.

Generation of Additional ribB Mutants.

Having established that three different mutations in the ribB gene can sustain growth of an *E. coli* dxs knockout we set out to find other ribB mutations that could also fill this role. A plasmid library of ribB mutants was constructed in pTrc99A, in which ribB is under control of the trc promoter, inducible by IPTG. Two different methods were used to mutagenize the ribB coding sequence: chemical mutagenesis using hydroxylamine (Rose M D, Fink G R, Cell. 1987 Mar. 27; 48(6):1047-60; hereby incorporated by reference), and error-prone PCR mutagenesis. The mutant libraries were transformed into the *E. coli* Δdxs pMBI strain and screened for growth on EZ-rich-xylose agar plates with no mevalonate. Plasmids were recovered from mevalonate-independent isolates and the ribB sequence was analyzed. Chemical mutagenesis using hydroxylamine yielded several ribB mutants that were capable of growth in the absence of mevalonate. The mutants were ranked in approximate order of their isolation date and relative size on agar plates (with ribB C1-C16 being the fastest growing colonies). As can be seen from Table 1, five different mutants were isolated, with most of them appearing several times. The G108S and T88I mutants were the fastest-growing isolates on EZ-rich-xylose agar plates. The G92D mutant isolated here was also discovered as a genomic mutant following selective pressure (above). The other two genomic ribB mutants that were isolated following selective pressure and genome sequencing (S89R and T106I) were not isolated following chemical mutagenesis of the plasmid-based ribB gene, perhaps due to limitations of the types of mutants that are likely to arise from use of the hydroxylamine mutagen. However, mutants were isolated in neighboring amino acids (T88I, G108S, and V109I), suggesting that this region of the protein, spanning approximately from positions 80 to 120 in the amino acid sequence, may be most important for generation of the novel RibB enzyme activity that enables mevalonate-independent growth. In summary, a total of seven ribB mutants have been found to enable mevalonate-independent growth in the *E. coli* Δdxs pMBI strain: G108S, T88I, S89R, V109I, M182I, G92D, and T106I. They were isolated either through directed evolution of strains isolated following selective pressure on mevalonate, or via direct mutagenesis of the ribB gene.

Expression of yajO and xylB.

In order to investigate whether the *E. coli* gene yajO is capable of playing a role in DXP biosynthesis we expressed the native yajO coding sequence under control of the trc promoter on the plasmid pTrc99A. We found that expression of yajO could support mevalonate-independent growth when expressed in the parent *E. coli* Δdxs pMBI strain, although it does not complement the dxs knockout as fully as the ribB mutants. Increasing yajO expression levels through substitution of a stronger ribosome site (rbs) sequence on the plasmid appeared to improve the mevalonate-independent growth rate in the *E. coli* Δdxs strain. It was observed that a metabolic adaptation appeared to take place in Δdxs pMBI cells expressing yajO, resulting in improvements in mevalonate-independent growth, and we hypothesized that there may be an additional *E. coli* gene involved in DXP biosynthesis besides yajO. Following the theory that YajO may be capable of synthesizing 1-deoxyxylulose (DX), we reasoned that the native *E. coli* xylulokinase XylB may complete the pathway to DXP as it has been demonstrated previously to convert DX to DXP (Wungsintaweekul et al., 2001). Upon co-expression of both the yajO and xylB genes we observed a further increase in the mevalonate-independent growth rate of *E. coli* Δdxs pMBI when grown on EZ-rich-xylose agar plates.

Comparison of Growth in Defined Media.

Growth comparisons were made between the parent *E. coli* Δdxs pMBI strain and strains derived from it that contain either genomic ribB mutations, or plasmids harboring ribB mutants or yajO/xylB. Defined media was used in each case; EZ-rich or M9 media containing either xylose or glucose as carbon source. Growth was monitored in the absence or presence of exogenously added mevalonate.

Measurement of Isoprenoid Production.

In order to evaluate the impact of ribB mutants on isoprenoid production, *E. coli* Δdxs pMBI strains with or without the G92D mutation in the genomic ribB gene were transformed with pADS (Martin et al., 2003) a plasmid harboring amorphadiene synthase, a sesquiterpene synthase of plant origin. Growth was performed in M9 medium with either glucose or xylose as carbon source and with or without 0.1 mM mevalonate. An overlay of dodecane (10% of the culture volume) was added to each culture to trap the amorphadiene product. Samples were taken at intervals and analyzed by gas chromatography-mass spectrometry (GC-MS) to measure amorphadiene production.

TABLE 1

Isolation of ribB mutants capable of supporting mevalonate-independent growth in *E. coli* Δdxs pMBI.

| Mutant | Mutation in ribB |
|---|---|
| ribB C1 | G108S |
| ribB C2 | G108S |
| ribB C3 | G108S |
| ribB C4 | G108S |
| ribB C5 | G108S |
| ribB C6 | T88I |
| ribB C7 | T88I |
| ribB C8 | T88I |
| ribB C9 | T88I |
| ribB C10 | G108S |
| ribB C11 | T88I |
| ribB C12 | G108S |
| ribB C13 | G108S |
| ribB C14 | G108S |
| ribB C15 | G108S |
| ribB C16 | G108S |
| ribB C17 | G108S |
| ribB C18 | T88I |
| ribB C19 | T88I |
| ribB C20 | T88I |
| ribB C21 | G108S |
| ribB C22 | G108S |
| ribB C23 | T88I |
| ribB C24 | V109I |
| ribB C25 | T88I |
| ribB C26 | T88I |
| ribB C27 | V109I |

TABLE 1-continued

Isolation of ribB mutants capable of supporting mevalonate-independent growth in *E. coli* Δdxs pMBI.

| Mutant | Mutation in ribB |
|---|---|
| ribB C28 | G108S |
| ribB C29 | T88I |
| ribB C30 | V109I |
| ribB C31 | M182I |
| ribB C32 | M182I |
| ribB C33 | M182I |
| ribB C34 | M182I |
| ribB C35 | V109I |
| ribB C36 | M182I |
| ribB C37 | T88I |
| ribB C38 | M182I |
| ribB C39 | M182I |
| ribB C40 | T88I |
| ribB C41 | T88I |
| ribB C42 | T88I |
| ribB C43 | M182I |
| ribB C44 | G92D |
| ribB C45 | T88I |
| ribB C46 | V109I |
| ribB C47 | M182I |
| ribB C48 | M182I |

Example 2

Figure 7:
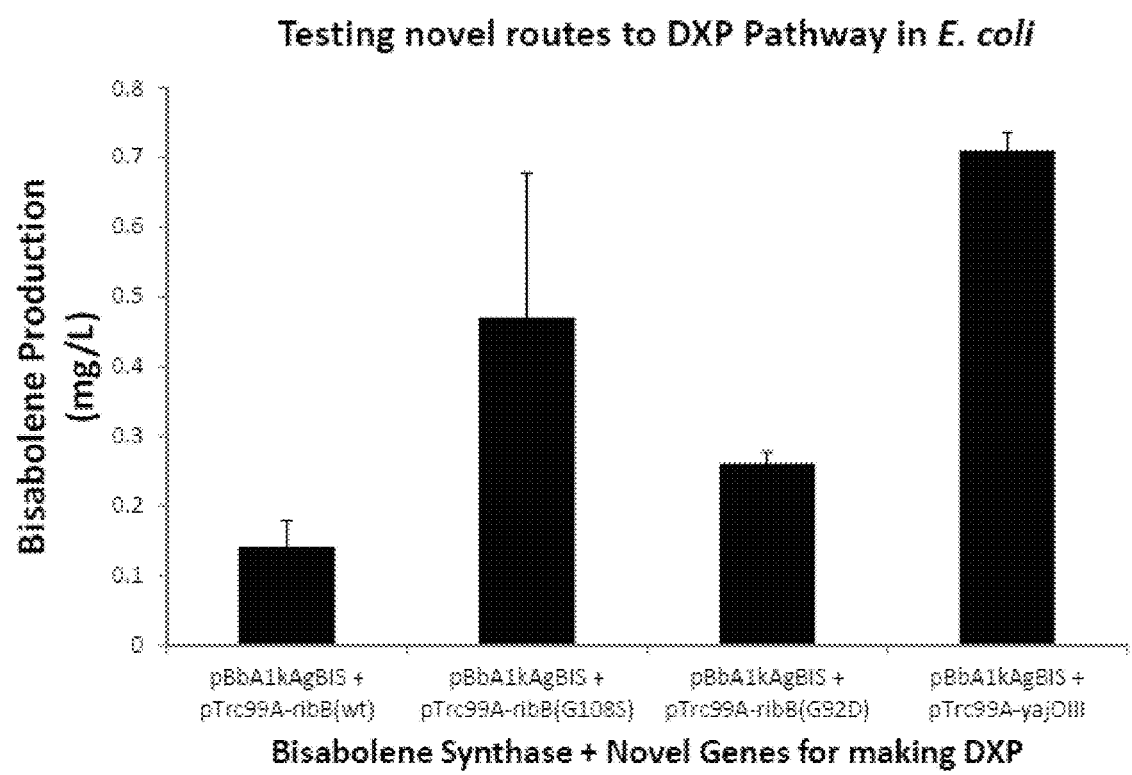
FIG. 7 shows results from an experiment to test the benefit from expression of either ribB mutants or the yajO gene for increasing isoprenoid production via the DXP pathway.

FIG. 7 shows results from an experiment carried out to test the benefit from expression of either ribB mutants or the yajO gene for increasing isoprenoid production via the DXP pathway. *E. coli* DH1 cells are transformed with two plasmids. In each case, the first plasmid harbors the bisabolene synthase gene from *Abies grandis* for the production of the isoprenoid bisabolene, which can be used as a biofuel. The second plasmid contains either a wild type version of the ribB gene (as a control), a mutant version of ribB (G108S or G92D), or the *E. coli* yajO gene as follows:

1. pBbA1kAgBIS+pTrc99A-ribB(wt)
2. pBbA1kAgBIS+pTrc99A-ribB(G108S)
3. pBbA1kAgBIS+pTrc99A-ribB(G92D)
4. pBbA1kAgBIS+pTrc99A-yajOIII The plasmid pBbA1kAgBIS is constructed as follows: the codon-optimized bisabolene synthase gene from *Abies grandis* (Pamela P. Peralta-Yahya, Mario Ouellet, Rossana Chan, Aindrila Mukhopadhyay, Jay D. Keasling, Taek Soon Lee, Identification and microbial production of a terpene-based advanced biofuel, *Nat Commun*. 2011 Sep. 27; 2: 483) is cloned between the EcoRI and BamHI sites of the pBbA1k plasmid (Taek Soon Lee, Rachel A Krupa, Fuzhong Zhang, Meghdad Hajimorad, William J Holtz, Nilu Prasad, Sung Kuk Lee, Jay D Keasling, BglBrick vectors and datasheets: A synthetic biology platform for gene expression, *J Biol Eng*. 2011; 5: 12) incorporating a strong ribosome binding site. The ribB wild type gene is amplified from *Escherichia coli* DH5α and cloned between the NcoI and HindIII sites of the common expression vector pTrc99A to make pTrc99A-ribB(wt). The plasmid pTrc99A-ribB(G108S) is identical to pTrc99A-ribB(wt) except that the glycine at position 108 is a serine. The plasmid pTrc99A-ribB(G92D) is identical to pTrc99A-ribB(wt) except that the glycine at position 92 is an aspartate. The yajO gene is amplified from *Escherichia coli* DH5α and cloned into the common expression vector pTrc99A to make pTrc99A-yajOIII.

The resulting strains are then grown (using three independent transformants for each) in EZ-Rich medium with xylose as carbon source. Bisabolene production is measured after three days of growth and is shown in FIG. 7. The first strain, containing the ribB wild type gene is a control to show production levels resulting from flux through the native DXP pathway alone. Relative to this strain, the stains containing ribB mutant genes and the yajO gene produce significantly more bisabolene. The strain containing the rib (G108S) mutant produces approximately 3.3-fold more bisabolene, while the strain containing the less effective ribB (G92D) mutant produces about 1.8-fold more bisabolene. Expression of the yajO gene (in this case the plasmid does not contain the xylB gene since *E. coli* expresses its native XylB enzyme when grown on xylose) yields 5-fold more bisabolene compared to the control strain.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A method of producing a 1-deoxyxylulose 5-phosphate or 1-deoxy-D-xylulose 5-phosphate (DXP) or a DXP derived compound, comprising:
   (a) providing a genetically modified host cell capable of producing 1-deoxyxylulose 5-phosphate or 1-deoxy-D-xylulose 5-phosphate (DXP) comprising: a mutant 3,4-dihydroxy-2-butanone 4-phosphate synthase (RibB) comprising a polypeptide sequence that (i) is at least 90% identical to SEQ ID NO:1, and (ii) comprises one or more of the following amino acid substitutions corresponding to substitutions in SEQ ID NO:1 selected from the group consisting of G108S, T88I, S89R, V109I, M182I, G92D, and T106I;
   (b) culturing the genetically modified host cell in a medium under a suitable condition such that the culturing results in the genetically modified host cell producing the DXP or the DXP derived compound, and (c) optionally recovering the DXP or the DXP derived compound from the medium, wherein the recovering step is concurrent or subsequent to the culturing step; wherein the host cell is a prokaryotic cell.

2. The method of claim 1, wherein the mutant RibB comprises a polypeptide sequence that is at least 95% identical to SEQ ID NO:1.

3. The method of claim 2, wherein the mutant RibB comprises a polypeptide sequence that is at least 99% identical to SEQ ID NO:1.

4. The method of claim 1, wherein the host cell does not naturally comprise a gene encoding a 1-deoxy-d-xylulose 5-phosphate synthase (Dxs).

5. The method of claim 1, wherein the host cell (a) further comprises a disruption in an endogenous gene encoding a 1-deoxy-D-xylulose 5-phosphate synthase, or (b) further comprises a mutation in an endogenous gene encoding 1-deoxy-D-xylulose 5-phosphate synthase which reduces 1-deoxy-D-xylulose 5-phosphate synthase activity or reduces expression of said gene.

6. The method of claim 1, wherein the host cell is capable of producing 2C-methyl-D-erythritol 4-phosphate, and the host cell further comprises a 2C-methyl-D-erythritol 4-phosphate synthase.

7. The method of claim 1, wherein the host cell is capable of producing 4-diphosphocytidyl-2C-methyl-D-erythritol, and the host cell further comprises a 2C-methyl-D-erythritol 4-phosphate synthase and a 4-diphosphocytidyl-2C-methyl-D-erythritol 4-phosphate synthase.

8. The method of claim 1, wherein the host cell is capable of producing 4-diphosphocytidyl-2C-methyl-D-erythritol 2-phosphate, and the host cell further comprises a 2C-methyl-D-erythritol 4-phosphate synthase, a 4-diphosphocytidyl-2C-methyl-D-erythritol 4-phosphate synthase, and a 4-diphosphocytidyl-2C-methyl-D-erythritol kinase.

9. The method of claim 1, wherein the host cell is capable of producing 2C-methyl-D-erythritol 2,4-diphosphate, and the host cell further comprises a 2C-methyl-D-erythritol 4-phosphate synthase, a 4-diphosphocytidyl-2C-methyl-D-erythritol 4-phosphate synthase, a 4-diphosphocytidyl-2C-methyl-D-erythritol kinase, and a 2C-methyl-D-erythritol 2,4-diphosphate synthase.

10. The method of claim 1, wherein the host cell is capable of producing 1-hydroxy-2-methyl-2-(E)-butenyl 4-diphosphate, and the host cell further comprises a 2C-methyl-D-erythritol 4-phosphate synthase, a 4-diphosphocytidyl-2C-methyl-D-erythritol 4-phosphate synthase, a 4-diphosphocytidyl-2C-methyl-D-erythritol kinase, a 2C-methyl-D-erythritol 2,4-diphosphate synthase, and a 2C-methyl-D-erythritol 2,4-cyclodiphosphate reductase.

11. The method of claim 1, wherein the host cell is capable of producing isopentenyl pyrophosphate (IPP) and/or dimethylallyl pyrophosphate (DMAPP), and the host cell further comprises a 2C-methyl-D-erythritol 4-phosphate synthase, a 4-diphosphocytidyl-2C-methyl-D-erythritol 4-phosphate synthase, a 4-diphosphocytidyl-2C-methyl-D-erythritol kinase, a 2C-methyl-D-erythritol 2,4-diphosphate synthase, a 2C-methyl-D-erythritol 2,4-cyclodiphosphate reductase, and a 1-hydroxy-2-methyl-butenyl 4-diphosphate reductase.

12. The method of claim 1, wherein the host cell is capable of producing geranyl pyrophosphate (GPP) and optionally farnesyl pyrophosphate (FPP), and the host cell further comprises a 2C-methyl-D-erythritol 4-phosphate synthase, a 4-diphosphocytidyl-2C-methyl-D-erythritol 4-phosphate synthase, a 4-diphosphocytidyl-2C-methyl-D-erythritol kinase, a 2C-methyl-D-erythritol 2,4-diphosphate synthase, a 2C-methyl-D-erythritol 2,4-cyclodiphosphate reductase, a 1-hydroxy-2-methyl-butenyl 4-diphosphate reductase, a GPP synthase and optionally a FPP synthase.

13. The method of claim 1, wherein the host cell is capable of producing DXP derivatives, wherein said DXP derivatives are (i) isopentenol, geraniol, and optionally farnesol, or (ii) an isoprenyl alkanoate, and the host cell further comprises a 2C-methyl-D-erythritol 4-phosphate synthase, a 4-diphosphocytidyl-2C-methyl-D-erythritol 4-phosphate synthase, a 4-diphosphocytidyl-2C-methyl-D-erythritol kinase, a 2C-methyl-D-erythritol 2,4-diphosphate synthase, a 2C-methyl-D-erythritol 2,4-cyclodiphosphate reductase, a 1-hydroxy-2-methyl-butenyl 4-diphosphate reductase, a GPP synthase, the corresponding enzymes for producing said DXP derivatives of (i) or (ii), and optionally comprises a FPP synthase.

14. The method of claim 1, wherein the host cell is a prokaryotic cell.

15. The method of claim 14, wherein the prokaryotic cell is a microorganism from the genus *Escherichia, Salmonella, Vibrio, Pasteurella, Haemophilus*, or *Pseudomonas*.

16. The method of claim 15, wherein the prokaryotic cell is an *Escherichia coli* cell.

17. A method of producing a 1-deoxyxylulose 5-phosphate or 1-deoxy-D-xylulose 5-phosphate (DXP) or a DXP derived compound, comprising:
 (a) providing a genetically modified host cell capable of producing 1-deoxyxylulose 5-phosphate or 1-deoxy-D-xylulose 5-phosphate (DXP) comprising: an aldo/keto reductase (YajO) comprising a polypeptide sequence that is at least 90% identical to SEQ ID NO:2, and a xylulokinase (XylB) comprising a polypeptide sequence that is at least 90% identical to SEQ ID NO:3; wherein the host cell: (i) does not naturally encode a gene encoding a 1-deoxy-d-xylulose 5-phosphate synthase, or (ii) further comprises a disruption in an endogenous gene encoding a 1-deoxy-D-xylulose 5-phosphate synthase, and wherein:
  (I) the host cell is capable of producing GPP and optionally FPP, and the host cell further comprises a 2C-methyl-D-erythritol 4-phosphate synthase, a 4-diphosphocytidyl-2C-methyl-D-erythritol 4-phosphate synthase, a 4-diphosphocytidyl-2C-methyl-D-erythritol kinase, a 2C-methyl-D-erythritol 2,4-diphosphate synthase, a 2C-methyl-D-erythritol 2,4-cyclodiphosphate reductase, a 1-hydroxy-2-methyl-butenyl 4-diphosphate reductase, a GPP synthase and optionally a FPP synthase; or
  (II) the host cell is capable of producing the DXP derived compound, wherein said DXP derived compound is (i) isopentenol, geraniol, and optionally farnesol, or (ii) an isoprenyl alkanoate, and the host cell further comprises a 2C-methyl-D-erythritol 4-phosphate synthase, a 4-diphosphocytidyl-2C-methyl-D-erythritol 4-phosphate synthase, a 4-diphosphocytidyl-2C-methyl-D-erythritol kinase, a 2C-methyl-D-erythritol 2,4-diphosphate synthase, a 2C-methyl-D-erythritol 2,4-cyclodiphosphate reductase, a 1-hydroxy-2-methyl-butenyl 4-diphosphate reductase, a GPP synthase, the corresponding enzymes for producing said DXP derived compound of (i) or (ii), and optionally comprises a FPP synthase;
 (b) culturing the genetically modified host cell in a medium under a suitable condition such that the culturing results in the genetically modified host cell producing the DXP or the DXP derived compound, and (c) optionally recovering the DXP or the DXP derived compound from the medium, wherein the recovering step is concurrent or subsequent to the culturing step; wherein the host cell is a prokaryotic cell.

18. The method of claim 17, wherein the YajO comprises a polypeptide sequence that is at least 95% identical to SEQ ID NO:2, and the XylB comprises a polypeptide sequence that is at least 95% identical to SEQ ID NO:3.

19. The method of claim 18, wherein the YajO comprises a polypeptide sequence that is at least 99% identical to SEQ ID NO:2, and the XylB comprises a polypeptide sequence that is at least 99% identical to SEQ ID NO:3.

20. The method of claim 17, wherein the host cell is capable of producing 2C-methyl-D-erythritol 4-phosphate, and the host cell further comprises a 2C-methyl-D-erythritol 4-phosphate synthase.

21. The method of claim 17, wherein the host cell is capable of producing 4-diphosphocytidyl-2C-methyl-D-erythritol, and the host cell further comprises a 2C-methyl-D-erythritol 4-phosphate synthase and a 4-diphosphocytidyl-2C-methyl-D-erythritol 4-phosphate synthase.

22. The method of claim 17, wherein the host cell is capable of producing 4-diphosphocytidyl-2C-methyl-D-erythritol 2-phosphate, and the host cell further comprises a 2C-methyl-D-erythritol 4-phosphate synthase, a 4-diphosphocytidyl-2C-methyl-D-erythritol 4-phosphate synthase, and a 4-diphosphocytidyl-2C-methyl-D-erythritol kinase.

23. The method of claim 17, wherein the host cell is capable of producing 2C-methyl-D-erythritol 2,4-diphosphate, and the host cell further comprises a 2C-methyl-D-erythritol 4-phosphate synthase, a 4-diphosphocytidyl-2C-methyl-D-erythritol 4-phosphate synthase, a 4-diphosphocytidyl-2C-methyl-D-erythritol kinase, and a 2C-methyl-D-erythritol 2,4-diphosphate synthase.

24. The method of claim 17, wherein the host cell is capable of producing 1-hydroxy-2-methyl-2-(E)-butenyl 4-diphosphate, and the host cell further comprises a 2C-methyl-D-erythritol 4-phosphate synthase, a 4-diphosphocytidyl-2C-methyl-D-erythritol 4-phosphate synthase, a 4-diphosphocytidyl-2C-methyl-D-erythritol kinase, a 2C-methyl-D-erythritol 2,4-diphosphate synthase, and a 2C-methyl-D-erythritol 2,4-cyclodiphosphate reductase.

25. The method of claim 17, wherein the host cell is capable of producing IPP and/or DMAPP, and the host cell further comprises a 2C-methyl-D-erythritol 4-phosphate synthase, a 4-diphosphocytidyl-2C-methyl-D-erythritol 4-phosphate synthase, a 4-diphosphocytidyl-2C-methyl-D-erythritol kinase, a 2C-methyl-D-erythritol 2,4-diphosphate synthase, a 2C-methyl-D-erythritol 2,4-cyclodiphosphate reductase, and a 1-hydroxy-2-methyl-butenyl 4-diphosphate reductase.

26. The method of claim 17, wherein the host cell is a prokaryotic cell.

27. The method of claim 26, wherein the prokaryotic cell is a microorganism from the genus *Escherichia, Salmonella, Vibrio, Pasteurella, Haemophilus*, or *Pseudomonas*.

28. The method of claim 27, wherein the prokaryotic cell is an *Escherichia coli* cell.

* * * * *